United States Patent [19]

Giobbio et al.

[11] 4,434,097
[45] Feb. 28, 1984

[54] PROCESS FOR THE REMOVAL OF THE FORMYL GROUP FROM N-FORMYL PEPTIDES AND ESTERS THEREOF

[75] Inventors: Vincenzo Giobbio, Turin; Giorgio Ornato; Livio Buracchi, both of Ivrea; Alberto Mangia, Milan, all of Italy

[73] Assignee: Pierrel S.p.A., Naples, Italy

[21] Appl. No.: 372,216

[22] Filed: Apr. 26, 1982

[30] Foreign Application Priority Data

May 13, 1981 [IT] Italy .................. 21674 A/81

[51] Int. Cl.³ .......................................... C07C 103/52
[52] U.S. Cl. ............................................ 260/112.5 R
[58] Field of Search .................. 424/177; 260/112.5 R

[56] References Cited

FOREIGN PATENT DOCUMENTS 1182450 2/1970 United Kingdom .

OTHER PUBLICATIONS

Chemical Abstracts, vol. 55, 1961, Abstract No. 18612b, (I).
Chemical Abstracts, vol. 70, 1969, Abst. No. 4596s, (II).
Chemical Abstracts, vol. 69, 1968, Abst. No. 67692v, (III).
Lefrancier et al., Mémories Présentés a la Société Chimique, Feb. 4, 1965, pp. 3668–3675.

Primary Examiner—Delbert R. Phillips
Assistant Examiner—F. Moezie
Attorney, Agent, or Firm—Bucknam and Archer

[57] ABSTRACT

A process for the removal of the formyl group in N-formylated peptides or their esters is described. The N-formyl compound is reacted with hydrazine or a substituted hydrazine of formula I:

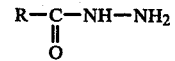

at a pH between 1 and 3.5, keeping the pH constant during the reaction. The process is particularly useful for the preparation of aspartam.

10 Claims, No Drawings

PROCESS FOR THE REMOVAL OF THE FORMYL GROUP FROM N-FORMYL PEPTIDES AND ESTERS THEREOF

This invention relates to peptides and more specifically to the elimination of the formyl group from peptides, or their N-formyl esters by means of hydrazine or derivatives of hydrazine under specific conditions of pH.

It is well known in the chemical literature that the amino group of amino acids may be blocked by means of the formyl residue in order to protect the amino group during the course of peptide syntheses. Obviously, at the end of the process, it is necessary to free the amino group by removing the formyl group. While the first step of the process, that is the formylation, may be carried out easily, the results which are obtained in the subsequent final step of deformylation by means of conventional methods are not equally satisfactory. In fact, although the conditions for the deformylation which are adopted commonly are quite simple, the results obtained frequently are deceiving because changes in the peptide molecule which are more or less substantial occur, changes which involve also even the peptide bond. This occurs when one operates under the usual deformylation conditions, that is in a solution of water and alcohol with alcohols which contain 1-5 carbon atoms, in the presence of strong acids such as hydrochloric acid, sulfuric acid, nitric acid, p-toluenesulfonic acid or trifluoroacetic acid.

The changes in the chemical structure mentioned hereinabove are even more clear when, instead of a formylated peptide, the substrate consists of a peptide which is formylated and esterified, because in addition to the difficulties mentioned hereinabove, frequently hydrolysis of the ester group also occurs to an extent which is more or less appreciable and the product is the corresponding diketopiperazine.

A substantial bibliography on the deformylation of peptides is found in: Zehra, A., Ber. 23, 3625 (1890); Hillmann-Elies, A., Naturforsch., 6 B, 340 (1951); Waley, S. G., Chem. Ind., 1953, 107; Boissonnas, R. A., Helv. Chim. Acta, 36, 875 (1953); Sheehan, J. C., J. Am. Chem. Soc. 80, 1154 (1958); other detailed descriptions are found in classical literature on peptides, such as J. Greenstein: Chem. of Am. Acids, II, 1244, 46 47). The same authors have investigated the deformylation carried out in an acidic medium.

More recently, other investigators have operated under different conditions and have achieved superior results utilizing as the deformylating agents other substances such as acetyl chloride or hydroxylamine or hydrazine. However, these authors have stated that the latter is not suitable for the deformylation of esters because it leads to the formation of the corresponding hydrazine derivatives. (Lefrancier, Bull. Soc. Chim. France 1965, 3668; Geiger, GB-PS 1 182 450).

Other investigators have deformylated peptides or esters of peptides by oxidation with $H_2O_2$ (Losse, Am. Chem. 1960, 636, 140) or by means of hydrogenolysis (Losse, J. Prakt. Chem. 1964, 24, 118).

The importance of the N-deformylation of peptides or their N-formylated esters, is clear also from the industrial point of view. One example of a substance with industrial importance having a peptide structure and having marked sweetening properties is α-L-aspartyl-L-phenylalanine methyl ester, which is known as "aspartam".

This substance has been prepared by many different methods using almost all the classical methods used for the preparation of peptides, and particularly by blocking the amino group of aspartic acid followed by activation of its α-carboxy group in the form of an active ester or anhydride, followed by a reaction of condensation with phenylalanine methyl ester and the removal of the group which blocks the amino group in the esterified peptide which has been obtained.

The industrial production processes for the preparation of α-L-aspartyl-L-phenalalanine methyl ester, have met with substantial practical difficulties due to the selection of the scheme to adopt, as well as due to the fact that several schemes involve the use of toxic substances, such as phosgene or substances of difficult utilization, such as carbobenzoxychloride. Another difficulty is that the schemes lead to the desired product in very low yields.

The industrial process, which appears to be relatively easier to carry out for the preparation of aspartam, involves the condensation of the anhydride of N-formyl-L-aspartic acid with L-phenylalanine methyl ester and the subsequent N-deformylation of N-formyl-α-L-aspartyl-L-phenylalanine methyl ester so obtained. The N-deformylation is carried out in the presence of a specific solvent and strong inorganic acids, according to Takemoto, German Offenlegungsschrift No. 2,635,948 or with hydroxylamine according to Takemoto, German Offenlegungsschrift No. 2,554,421 or by heating in the presence of water according to Takemoto, Japanese Kokai No. 76 39,602 or with hydrochloric acid in methanol according to German Offenlegungsschrift No. 2,256,055. The methods described in these publications offer several drawbacks, in general, in the reaction of deformylation of other N-formylated peptides or the respective esters. Above all, a drawback consists of the low yields, which are obtained in the final steps of the synthesis and the fact that the intermediates are quite expensive. In addition, the low yields are accompanied by substantial impurities in the final products, which obviously must be purified further with substantial additional production costs.

It has now been found surprisingly that the elimination of the N-formyl residue in peptides or their respective esters may be carried out in a simple manner with surprising and substantial improved yields by carrying out the removal of the formyl group in the presence of hydrazine or hydrazine derivatives in the pH range between 1 and 3.5. The pH range is crucial for the reaction.

An object of the present invention is to provide a process for the elimination of the formyl group in N-formylated peptides or their respective esters, and particularly for the elimination of this group in the methyl ester of N-formyl-α-L-aspartyl-L-phenylalanine by means of hydrazine or hydrazine derivatives of formula I:

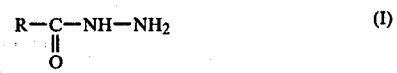

in which R is an alkyl residue of 1-5 carbon atoms, which may be saturated or unsaturated, linear or branched or a cycloalkyl residue or an aryl residue, which group may also be substituted by other functional groups or an amino group, the reaction being carried out at a pH between 1 and 3.5.

In the process according to the present invention, the pH must be between 1 and 3.5. Indeed, if one carries out the reaction with acids in the absence of hydrazine or hydrazine derivatives, one notes that if the reaction is carried out at a pH lower than 1, after one hour at 60° C., the formyl ester starting material has completely disappeared and a small yield, about 15%, of a deformylated product is formed. By means of TLC (thin layer chromatography), one notes a substantial amount of a product, which has been found to be diketopiperazine, (see below).

If, on the other hand, one carries out the reaction at a pH higher than 3.5, the deformylation occurs to a very small, almost insignificant extent, even by carrying out the reaction for a very substantial period of time. The pH range within which it is necessary to carry out the reaction, therefore, must be maintained constant during the course of the reaction because, when the base is set free, the pH has a tendency to increase. This control may be carried out by adding gradually to the reaction mixture, a solution of an inorganic acid, such as for instance, a solution of 10% of hydrochloric acid, or sulfuric acid or also paratoluenesulfonic acid. It is also possible to use suitable buffered solutions.

It has already been discussed hereinabove that other investigators have reported that hydrazine is not suitable for the deformylation of N-formylated peptide esters due to the possible formation of the corresponding hydrazides (P. Lefrancier, et al, Bull. Soc. Chim. France 1965, 3668).

However, it has been found surprisingly that this drawback may be minimized if one carries out the reaction according to the present invention in the pH range between 1 and 3.5. By reference to the experimental conditions, the quantity of hydrazine may be varied between 1 and 3 moles for each mole of the peptide or the corresponding esters to be deformylated, while the solvent is methanol or a mixture of methanol and water or other solvents, the structure and the quantity of the solvents themselves being of little significance. In any event, in order to carry out the process satisfactorily, it is necessary, as already mentioned hereinabove, to adjust initially the pH of the mixture to between 1 and 3.5 and maintain this pH range during the course of the reaction, which may be carried out at a temperature between 20° and 100° C., obviously with a different reaction time, depending upon the temperature. The acid being utilized may be a strong mineral acid, such as hydrochloric acid or sulfuric acid or nitric or it may be paratoluenesulfonic acid.

It has been found that the N-deformylation occurs with improved yields, if the reaction is carried out in the presence of substances of structure

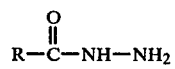

in which R has the meaning described hereinabove. The reaction itself proceeds very easily under conditions of minimum changes and with very good yields, which vary between 75% to 90% and even higher, depending on the substance being used. It has been observed that the activity of the substance of formula

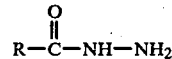

as the deformylating agents, is particularly greater in the case of acetylhydrazine, which is the simplest substance, benzoylhydrazine, trimethylaminoacetylhydrazide chloride, the latter being commonly called "Girard T", which is more complex and which contains additional functional groups and semicarbazide.

With reference to the experimental conditions, the quantity of the deformylating substances is between 1 and 5 moles with respect to one mole of the peptide or the ester being deformylated; it is possible to use also greater quantities of the reactant, but without a substantial economical advantage.

The solvent preferably is methanol or a mixture of methanol and water in the case of peptides, but in the case of peptide esters, it is preferably the same alcohol, which forms the ester in the peptide. Even here, the structure of the solvent is not significant, so that it is possible to use also another alcohol with a number of carbon atoms varying between 2 and 5 or other solvents, which are soluble in water, such as dioxane, acetone, acetonitrile, and dimethylformamide. It is also possible to use other solvents, which are not soluble in water such as hydrocarbons, chlorinated hydrocarbons, ethers, ketones, esters or mixtures of these solvents. All these solvents may be used in the presence or absence of water and, therefore, in some instances, a single phase may be present and in other instances, two phases may be present. The reaction temperature is not crucial because the temperature only influences the reaction time. More specifically, the temperature may vary between 20° and 150° C., depending upon the solvent being used and the reaction time may vary between thirty minutes and thirty hours depending upon the temperature. The examples which follow hereinbelow in detail, illustrate the process according to the present invention under different experimental conditions without, however, limitation of the scope of the invention. The progress of the reaction is, in general, controlled very well by means of TLC (thin layer chromatography), which in addition demonstrates clearly the low changes in chemical structure which result during the course of the reaction. In fact, it is possible to note clearly, in addition to the deformylated product, only the presence of small quantities of a "diketopiperazine". This substance, specifically 2-benzyl-3,6-diketo-5-piperazinylacetic acid, normally is present in the commercial aspartam in the amount of 2% and in fact, the Food and Drug Administration, Title 21, Code of Federal Regulations, Paragraph 121.1258, prescribes a maximum limit of 2% for this substance in aspartam. In the tests of the purity of aspartam obtained according to the process of the present invention, which tests have been carried out by means of HPLC (high pressure liquid chromatography), this substance, the substituted diketopiperazine, mentioned hereinabove, has never been above 0.6–0.7%. Similar improvement with respect to the commercial preparations has been achieved with respect to another impurity normally found in aspartam, that is α-aspartyl-phenylalanine, which in commercial samples of aspartam is present in the amount of about 1%, while in the product obtained according to the present invention, is never in excess of 0.3%. The quantitative evaluation of the product of the reaction has

EXAMPLE 1

N-formyl-α-L-aspartyl-L-phenylalanine methylester, 3.2 grams (10 millimoles), is dissolved in 32 cc of methanol. There is added 3.2 cc of water and then the pH is adjusted to 2 with 0.5 cc of 3% hydrochloric acid. The solution is heated to 70° C. and this temperature is kept for 10 hours while the pH is continuously adjusted by means of 3% hydrochloric acid so as to keep the pH in the range of 1.5–3.0.
Control TLC (eluent: methylethylketone/acetic acid/pyridine/water, 32-4-2-6)
Ninhydrin indicator:
  One large spot: Rf 0.35 (aspartam)
  One spot: Rf 0.1 (deformylated and demethylated peptide)
  One spot undetermined: Rf 0.9
Analysis GLC: α-L-aspartyl-L-phenylalanine methylester 1.91 grams (Yield: 65%)

EXAMPLE 2

N-formyl-α-L-aspartyl-L-phenylalanine methylester, 3.2 grams (10 millimoles), is dissolved in 32 cc of methanol. Separately, a solution of 1.5 grams of hydrazine monohydrate (30 millimoles), dissolved in 5 cc of water is prepared and the pH is adjusted to 1.5 with 15% hydrochloric acid. This solution is added to the first solution and the pH is adjusted to 1.5 with 15% hydrochloric acid. The solution is heated to 70° C. and this temperature is maintained for 7.5 hours, while keeping the pH always between 1.5 and 3.5 by the addition of 15% of hydrochloric acid).
Analysis GLC: α-L-aspartyl-L-phenylalanine methylester: 2 grams (Yield: 70%).

EXAMPLE 3

N-formyl-α-L-aspartyl-L-phenylalanine methylester, 3.2 grams (10 millimoles), is dissolved in 32 cc of methanol. There is added 3.2 cc of water and 2.2 grams of acetylhydrazine, (30 millimoles). The pH is adjusted to 2.5 with a 10% hydrochloric acid solution. The mixture is heated to 70° C. and is kept for six hours, at this temperature while keeping the pH between 1.5 and 3.5.
Control TLC (eluent: methylethylketone/acetic acid/pyridine/water 32-4-2-6)
Ninhydrin indicator:
  1 spot: Rf 0.35 (aspartam)
  1 spot, very weak: Rf 0.1 (deformylated and demethylated peptide)
Analysis GLC: α-L-aspartyl-L-phenylalanine methylester 2.65 grams (Yield: 90%).

EXAMPLE 4

N-formyl-α-L-aspartyl-L-phenylalanine methylester, 3.2 grams, (10 millimoles) is dissolved in 32 ml of methanol. There is added 3.2 cc of water and 5 grams of "Girard T" reagent, 30 millimoles and the pH is adjusted to 2.5 with 10% hydrochloric solution. The mixture is heated to 70° C. and kept at this temperature for 7 hours, keeping the pH between 1.5 and 3.5
Control TLC (Eluent: methylethylketone/acetic acid/pyridine/water 32-4-2-6)
Ninhydrin Indicator:
  1 Spot: Rf 0.35 (aspartam)
  1 Weak Spot: Rf 0.1 (deformylated and demethylated peptide)
Analysis GLC: α-L-aspartyl-L-phenylalanine methylester 2.2 grams (Yield: 76%).

EXAMPLE 5

N-formyl-α-L-aspartyl-L-phenylalanine methylester, 3.2 grams, (10 millimoles), is dissolved in 32 cc of methanol; there is added 3.2 millimoles of water and 3.33 grams of semicarbazide hydrochloride, that is 30 millimoles. The pH is 2 and there is no need to correct the pH. The mixture is warmed to 70° C. and kept at this temperature for 8 hours, keeping the pH between 1.5 and 3.5.
Analysis GLC: α-L-aspartyl-L-phenylalanine methylester 2.4 grams (Yield: 83%).

EXAMPLE 6

N-formyl-α-L-aspartyl-L-phenylalanine methylester, 3.2 grams, (10 millimoles), is dissolved in 32 cc of methanol. There is added 3.2 cc of water and 4 grams of benzoylhydrazide, (30 millimoles). The pH is adjusted to 1.5–3.5. The solution is heated to 70° C. and kept at this temperature for 4 hours, keeping the pH in the prescribed range. The material is evaporated under vacuum at a temperature lower than 40° C.; 10 cc of water is added, the pH is adjusted to the isoelectric point, (pH=5.2), cooled to 0° C. and filtered with suction. The product is 2.5 grams of aspartam, which is analytically pure. (Yield: 85.4%).

EXAMPLE 7

N-formyl-α-L-aspartyl-L-phenylalanine methylester, 12.825 kg, is dissolved in 30 liters of dichloroethane to which is added 10 liters of glacial acetic acid, 10 liters of methanol and 14 kg of acetylhydrazine. The temperature is raised to 64° C. and the pH is adjusted to 2.2–2.3 by addition of a solution of concentrated hydrochloric acid. The solution is heated at 64° C. while always maintaining the pH in the range of 2.2–2.3; under these conditions the deformylation reaction is completed in the period of five hours. The final volume is 80 liters. The reaction solution is used to determine by analysis (HPLC, high pressure liquid chromatography) the content of α-L-aspartyl-L-phenylalanine methylester. The value is 132 mg/cc. The analytical conditions are as follows:
Column: $RP_8$ 10 microns, temperature of the column is 45° C., rate of flow is 2 cc/minute with UV at 215 nm as the indicator.
Eluent: phosphate buffer of pH of 7.5, 0.01 M/acetonitrile lichrosolv=9/1
The period of retention time of α-L-aspartyl-L-phenylalanine methylester: 5.2 min.
Yield of α-L-aspartyl-L-phenylalanine methyl ester is 10.55 kg (90%).
Dichloroethane and methanol are removed under vacuum, 50 liters of water are added and the pH is adjusted to 5.2, which is the isoelectric point of precipitation of aspartam. After cooling with brine to −5° C. for 10 hours, aspartam is centrifuged and well washed. After drying at 45° C. in a current of air, there is obtained 9 kg of aspartam with the following qualitative data.
Titer (HPLC): 99.3 dry
Substituted diketopiperazine (2-benzyl-3,6-diketo-5-piperazinylacetic acid): 0.5%
N-L-α-Aspartyl-L-phenylalanine (demethylated aspartam): 0.1%.

The mother liquid, containing about 1.5 kg of aspartam, is recycled during the subsequent work-up permitting practically almost quantitative recovery of the product aspartam.

Two commercial samples of different origin have given the following analytical data.
Sample "A": Titer (HPLC) 98.4%; "diketopiperazine", 0.7%; demethylated aspartam 2.1%.
Sample "B": Titer (HPLC) 97.0%; "diketopiperazine", 2.74%; demethylated aspartam 0.45%.

On the finished product, the analytical conditions of HPLC are as follows:
Column: lichrosorb $RP_{18}$, 10 microns, length 25 cm, internal diameter 4 mm.
Eluent: phosphate buffer pH 4 in methanol: 60/40 per titer of aspartam; 75-25 for the determination of impurities
Flow: 2 cc/minutes
Indicator: UV at 210 nm.
Period of Retention:
  Aspartam: 12.8 minutes (3.6 minutes in the determination of the titer.)
  Substituted Diketopiperazine: 5.1 minutes
  Demethylated Aspartam: 3.3 minutes

What is claimed is:

1. A process for the removal of the formyl group in a compound which contains an N-formyl group of formula NH—CHO and the compound is a peptide containing an ester group and wherein the —NH group of the NH—CHO group is attached to a carbon atom adjacent to the —CONH— grouping of said peptide, which consists of reacting said compound with hydrazine or a substituted hydrazine of formula I:

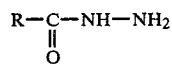

wherein R is a saturated or unsaturated, linear or branched, substituted or unsubstituted alkyl of 1-5 carbon atoms, or substituted or unsubstituted cycloalkyl or substituted or unsubstituted aryl or an amino group at a pH between 1 and 3.5, keeping the pH constant during the reaction, wherein the N-formyl group is removed while the ester group is not attacked, and isolating the ester of the N-deformylated peptide from the reaction mixture.

2. The process according to claim 1 wherein the pH is maintained constant at 1-3.5 during the reaction by addition of an inorganic acid or a buffer.

3. The process according to claim 1 wherein said hydrazine or said compound of formula I are used in the ratio of 1-5 moles per mole of said peptide or said ester of N-formylated peptide.

4. The process according to claim 1 wherein said compound of formula I is a member selected from the group consisting of acetyl hydrazide, benzoyl hydrazide, "Girard T", and semicarbazide.

5. The process according to claim 1 wherein the temperature during the reaction is between 20° and 150° C.

6. The process according to claim 1 wherein the reaction is carried out in a solvent comprising an alcohol of 1-5 carbon atoms.

7. The process according to claim 6 wherein water is added to said alcohol.

8. The process according to claims 6 or 7 wherein said solvent is a member selected from the group consisting of ketones, dimethylformamides, dimethylsulfoxide, acetonitrile, aliphatic esters, hydrocarbons, chlorinated hydrocarbons, and mixtures thereof.

9. The process according to claim 1 wherein said compound is the N-formyl-α-L-aspartyl-L-phenylalanine methylester and said N-deformylated compound is aspartam.

10. The process according to claim 9 wherein said substituted hydrazine is acetylhydrazine.

* * * * *